US007645595B2

(12) United States Patent
Amano et al.

(10) Patent No.: US 7,645,595 B2
(45) Date of Patent: Jan. 12, 2010

(54) METHOD OF PRODUCTION OF ARTIFICIAL SKIN

(75) Inventors: Satoshi Amano, Yokohama (JP); Yukiko Matsunaga, Yokohama (JP); Shinji Inomata, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 0 days.

(21) Appl. No.: 12/059,935

(22) Filed: Mar. 31, 2008

(65) Prior Publication Data

US 2008/0248571 A1    Oct. 9, 2008

Related U.S. Application Data (63) Continuation of application No. 11/304,886, filed on Dec. 16, 2005, now abandoned, which is a continuation of application No. 10/648,485, filed on Aug. 27, 2003, now abandoned, which is a continuation of application No. 09/979,712, filed as application No. PCT/JP01/02507 on Mar. 27, 2001, now abandoned.

(30) Foreign Application Priority Data

Mar. 27, 2000    (JP)    ............................ 2000-087574

(51) Int. Cl.
*C12N 15/09* (2006.01)
(52) U.S. Cl. ...................................... 435/69.2; 424/404
(58) Field of Classification Search ................ 435/69.2; 424/401, 404, 725; 514/844
See application file for complete search history.

(56) References Cited

U.S. PATENT DOCUMENTS

| 4,996,154 A | 2/1991 | Gabriels |
| 5,455,258 A | 10/1995 | MacPherson et al. |
| 5,595,885 A | 1/1997 | Stetler-Stevenson |
| 5,654,135 A | 8/1997 | Tinois et al. |
| 5,800,811 A * | 9/1998 | Hall et al. ................... 424/93.7 |
| 5,807,555 A | 9/1998 | Bonte et al. |
| 5,998,390 A | 12/1999 | Ramamurthy et al. |
| 6,093,398 A | 7/2000 | Khaw et al. |
| 6,110,208 A * | 8/2000 | Soranzo et al. .......... 623/15.12 |
| 6,146,664 A | 11/2000 | Siddiqui |
| 6,340,709 B1 | 1/2002 | Bocan et al. |
| 6,465,508 B1 | 10/2002 | Nelson et al. |
| 2002/0010162 A1 | 1/2002 | Fleischmajer |
| 2002/0188120 A1 | 12/2002 | Venkatesan et al. |
| 2004/0001897 A1 * | 1/2004 | Amano et al. ............... 424/745 |
| 2004/0033598 A1 * | 2/2004 | Vacanti et al. .............. 435/371 |
| 2004/0234510 A1 | 11/2004 | Mochitate |
| 2005/0085504 A1 | 4/2005 | Nelson et al. |
| 2005/0089516 A1 * | 4/2005 | Amano et al. ............ 424/94.64 |
| 2008/0241101 A1 * | 10/2008 | Amano et al. .............. 424/85.2 |

FOREIGN PATENT DOCUMENTS

| EP | 0 852 144 A2 | 7/1998 |
| EP | 0 852 144 A3 | 5/1999 |
| JP | 62-270162 | 11/1987 |
| JP | 01-158963 | 6/1989 |
| JP | 3-164168 | 7/1991 |
| JP | 06-345636 | 12/1994 |
| JP | 8-67621 | 3/1996 |
| JP | 8-196618 | 8/1996 |
| JP | 11-79970 | 3/1999 |
| JP | 11-079970 | 3/1999 |
| JP | 11-147833 | 6/1999 |
| JP | 11-315008 | 11/1999 |
| JP | 11-322577 | 11/1999 |
| JP | 11-343226 | 12/1999 |
| JP | 11-349436 | 12/1999 |
| JP | 2000-072653 | 3/2000 |
| WO | WO 89/05137 | 6/1989 |
| WO | WO 90/05755 | 5/1990 |
| WO | WO 95/24921 | 9/1995 |
| WO | WO 97/25969 | 7/1997 |
| WO | WO 99/03979 | 1/1999 |

OTHER PUBLICATIONS

Amano et al., "Importance of Balance Between Extracellular Matrix Synthesis and Degradation in Basement Membrane Formation," Exp. Cell. Res., 271(2):249-262, 2001.
Amano et al., "MMP inhibitors markedly enhance basement membrane formation in skin-equivalent model," J. Invest. Derm., 114(4):882, 2000.
Fisher et al., "Molecular basis of sun-induced premature skin aging and retinoid antagonism," Nature, 379:335-339, 1996.
Koivukangas et al., "UV irradiation induces the expression of gelatinases in human skin in vivo," Acta Derm Venereol., 74(4):279-282, 1994.
Lavker, "Structural alterations in exposed and unexposed aged skin," J. Invest. Dermatol., 73(1):59-66, 1979.
MacPherson et al., "Discovery of CGS 27023A, a non-peptidic, potent, and orally active stromelysin inhibitor that blocks cartilage degradation in rabbits," J. Med. Chem., 40(16):2525-2532, 1997.
Mish, ed., Merriam-Webster's Collegiate Dictionary, 1993, Merriam-Webster, Incorporated, Tenth Edition, p. 1205.
Moloney and Learn, "The effect of systemic cyclosporin A on a hairless mouse model of photoaging," Photochemistry and Photobiology, 56(4):495-504, 1992.
Odake et al., "Inhibition of matrix metalloproteinases by peptidyl hydroxamic acids," Biochem. Biophys. Res. Commun., 199(3):1442-1446, 1994.

(Continued)

*Primary Examiner*—Ralph Gitomer
(74) *Attorney, Agent, or Firm*—Fish & Richardson P.C.

(57) ABSTRACT

A method for production of artificial skin by administering matrix metalloproteinase inhibitor or matrix metalloproteinase inhibitor and matrix protein production promoting agent. The matrix metalloproteinase inhibitor is N-hydroxy-2(R)-[[(4-methoxyphenyl)sulfonyl](3-picolyl)amino]-3-methylbutanamide hydrochloride.

4 Claims, 4 Drawing Sheets

OTHER PUBLICATIONS

Pilcher et al., "Collagenase-1 and collagen in epidermal repair," Archives of Dermatol. Res., 290(6 Suppl):S37-46, 1998.

Scharffetter-Kochanek, "Photoaging of the connective tissue of skin: its prevention and therapy," Adv. Pharmacol.; 38:639-655, 1997.

Scott et al., "A matrix metalloproteinase inhibitor which prevents fibroblast-mediated collagen lattice contraction," Federation of European Biochemical Societies, 441(1):137-140, 1998.

Sidhu et al., "Curcumin enhances wound healing in streptozotocin induced diabetic rats and genetically diabetic mice," Wound Repair Regen., 7(5):362-374, 1999.

Tanaka et al., "Effects of Lysophospholipids on Hyaluronic Acid Synthesis in the Skin. I. Effects of Lysophosphatidylcholine on Hyaluronic Acid Sunthesis in Cultured Dermal Fibroblasts," J. Jap. Society of Fats and Oils, 46(9):13-19, 1997 (with English language abstract).

* cited by examiner

Fig. 1

CONTROL

CGS23027A
(10μM)

MMP-
Inhibitor
(300μM)

Fig.4
Skin Model (EM)

Control

CGS + SOYBEAN LECITHIN

METHOD OF PRODUCTION OF ARTIFICIAL SKIN

CROSS-REFERENCE TO RELATED APPLICATIONS

This application is a continuation of, and claims the benefit of priority under 35 U.S.C. § 120 of, U.S. patent application Ser. No. 11/304,886, filed on Dec. 16, 2005 (now abandoned), which is a continuation of U.S. patent application Ser. No. 10/648,485, filed on Aug. 27, 2003 (now abandoned), which is a continuation of U.S. patent application Ser. No. 09/979,712, filed on Nov. 26, 2001 (now abandoned), which is a U.S. national phase application filed under 35 U.S.C. § 371 of International Patent Application Number PCT/JP2001/002507, which was filed on Mar. 27, 2001, and which claims the benefit of the priority date of Japanese patent application number 2000-87574, filed on Mar. 27, 2000. The contents of all of these earlier-filed applications are hereby incorporated by reference herein in their entirety.

FIELD OF THE INVENTION

The present invention relates to a skin basement membrane stabilizing agent. In addition, the present invention relates to artificial skin formation promoting agent and a production method for artificial skin.

BACKGROUND ART

In the field of cosmetics and dermatology, a wide variety of measures have been proposed and attempted to alleviate or treat injuries caused by the effects of the external environment and aging including the exposure of the skin to sunlight. For example, examples of skin changes accompanying aging primarily include the formation of wrinkles, and hardening or decreased resiliency.

Primary interest is being directed at decreased function of collagen fibers and elastic fibers composed of collagen, elastin and glucosaminoglycans in the skin dermis as the cause of such changes. In the past, the use of hydroxycarboxylic acids (e.g., Japanese Patent No. 2533339), and the use of lysophospholipids (e.g., Japanese Unexamined Patent Publication No. 8-67621) or that described in the Journal of the Japan Society of Fats and Oils, Vol. 46, No. 9 (1997), pp. 13-19 have been proposed as means for preventing or repairing such changes.

In the former publication, keratin and wrinkles have been suggested as being able to be eradicated by preventing decreases in collagen fibers. On the other hand, in the latter publication, lysophospholipids are suggested to demonstrate whitening effects by accelerating the production ability of glycosaminoglycans (and more specifically, hyaluronic acid) in human fibroblasts.

The most powerful effect of the above external environment on skin aging is produced by ultraviolet rays present in sunlight, and these ultraviolet rays have clearly been established to be a factor that promotes aging. Ultraviolet rays are known to induce skin changes referred to as photoaging that is characterized by deep wrinkles (Scharffetter-Kochanek, Advances in Pharmacology, 1997, 58, 639-655). Ultraviolet rays have a diverse range of effects on the skin, including damage to genetic DNA, induced production of active oxygen, and more recently, induced production of matrix-metalloproteinases (Fisher, et al., Nature, 1996, 379, 335-339).

Due to the multifunctional nature of ultraviolet rays, the mechanism by which this photoaging induced by ultraviolet rays occurs has not been adequately elucidated. Deep wrinkles corresponding to human photoaged skin have been clearly shown to form on the skin on the backs of hairless mice following continuous irradiation of ultraviolet rays at an energy level not enough to cause erythema. Substances having an effect on wrinkles have also been evaluated using this mouse model (Moloney, et al., Photochem. Photobiol. 1992, 56, 495-504). However, the wrinkle formation mechanism has still not been adequately elucidated and its elucidation is awaited.

On the other hand, Koivukangas, et al. reported in 1994 that levels of gelatinase, an enzyme that decomposes the basement membrane, becomes elevated in skin irradiated with ultraviolet rays (Acta Derm. Venereol. 1994, 74, 279-282). In addition, it has also been reported that the basement membrane exhibits structural changes at sites of the skin exposed to sunlight, and that reduplication is observed particularly frequently (Lavker, J. Invest. Dermal. 1979, 73, 59-66). This suggests the possibility that ultraviolet rays contained in sunlight have an effect on basement membrane structure by increasing the amount of basement membrane decomposing enzymes produced in the skin.

However, there is no specific means known for promoting the formation of skin basement membrane structure.

Artificial skin is important as an alternative to natural skin that has been damaged by some cause, or as an experimental material for testing the action and pharmacological effects of pharmaceuticals and cosmetics on the skin. In either of these applications, artificial skin is desired that has a structure that imitates the structure of natural skin as closely as possible.

Natural skin is roughly composed of the epidermis, dermis and basement membrane present between them. One example of a known production method of artificial skin that imitates natural skin involves the formation of an epidermal layer by culturing normal human epidermal keratinocytes on contracted type I collagen gel having a structure that resembles the dermis and contains human fibroblasts. In this method, however, there was the problem of inadequate formation of a basement membrane between the collagen gel imitating the dermis and the epidermal layer imitating the epidermis.

DISCLOSURE OF THE INVENTION

Thus, the object of the present invention is to provide a novel means for stabilizing skin basement membrane, and to provide a novel means for achieving adequate formation of basement membrane in the production of artificial skin.

As a result of various studies to solve the above problems, the inventors of the present invention found that the formation of a skin basement membrane structure is promoted by administering matrix metalloproteinase inhibitor, or both matrix metalloproteinase inhibitor and matrix protein production promoting agent, thereby leading to completion of the present invention.

Thus, the present invention provides a skin basement membrane formation promoting agent that contains matrix metalloproteinase inhibitor.

In addition, the present invention provides a skin basement membrane formation promoting agent containing matrix metalloproteinase inhibitor and matrix protein production promoting agent.

As a result of various studies to solve the above problems, the inventors of the present invention found that, in culturing to produce artificial skin, formation of a basement membrane can be promoted by adding matrix metalloproteinase inhibitor, or both matrix metalloproteinase inhibitor and matrix protein production promoting agent to the medium, thereby leading to completion of the present invention.

Thus, the present invention provides an artificial skin formation promoting agent containing matrix metalloproteinase inhibitor.

In addition, the present invention provides an artificial skin formation promoting agent containing matrix metalloproteinase inhibitor and matrix protein production promoting agent.

In addition, the present invention provides an artificial skin production method comprising the addition of matrix metalloproteinase inhibitor to an artificial skin formation medium.

Moreover, the present invention provides an artificial skin production method comprising the addition of matrix metalloproteinase inhibitor and matrix protein production promoting agent to an artificial skin formation medium.

EMBODIMENTS FOR CARRYING OUT THE INVENTION

Matrix Metalloproteinase Inhibitor

There are no particular restrictions on the matrix metalloproteinase inhibitor used in the present invention, and any substance may be used provided it has such inhibitory activity. Examples of matrix metalloproteinase include gelatinase, collagenase, stromelysin and matrilysin. Thus, a substance (inhibiting) such as gelatinase, collagenase, stromelysin or matrilysin can be selected for the matrix metalloproteinase inhibitor.

Specific examples of matrix metalloproteinase inhibitors include substance CGS27023A N-hydroxy-2(R)-[[(4-methoxyphenyl)sulfonyl](3-picolyl)amino]-3-methylbutanamide hydrochloride (J. Med. Chem. 1997, Vol. 40, p. 2525-2532), and MMP-inhibitor (p-$NH_2$-Bz-Gly-Pro-D-Leu-Ala-NHOH) (FN-437) (BBRC, 1994, Vol. 199, p. 1442-1446).

Moreover, specific examples of metalloproteinase inhibitor of the present invention that can be used include various plant extracts and purified products obtained therefrom. Examples of such plants include *Thymus serpyllum* L., *Valeriana faureie* Briquet or other similar plants (Valerianaceae), *Diospyros kaki* Thunberg (Ebenaceae), *Astragalus sinicus* Linne (Leguminosae), *Crataegus cuneata* Siebold et Zuccarini (Rosaceae), *Paeonia suffruticosa* Andrews (*Poeonia montan* Sims) (Paconiaceae), *Thea sinensis* Linne var. *assamica* Pierre (Thcaccae), *Eucalyptus globulus* Labillardiere or its similar plants (Myrtaceae), *Potentilla tormentilla* Schrk (Rosaceae), *Tilia corda*:a Mill., *Tilia platyphyllus* Scop., *Tilia europaea* Linne (Tiliaceae), *Betula alba* Linne (Betulaceze), Origanummajorana L., *Uncaria gambir* Roxburgh (Rubiaceae), *Juglans regia* Linne var. *sinensis* De Candolie or its similar plants (Juglandaceae), *Sophora flavescens* Aiton (Leguminosae), *Sanguisorba officinalis* Linne (Rosaceae), *Hypericum perforatum* Linne or *Hypericum erectum* Thunberg (Guttiferae), *Thea sinensis* Linne (Theaceae), *Curcuma longa* L (Zingiberaceae), purified extracts of *Curcuma longa* L including *Symplocos racemosa* and *Cyperus rotundus, Cyperus scariosus, Gaultheria fragrantissima, Acacia formensia, Terminalia chebula, Ficus bengalensis, Cassia fistula* Linn, *Lyonia ovalifolia, Calophyllum inophyllum* and *Ficus religiosa*.

Extracts of these plants are obtained from the root, leaves, stem or flower in the case of herbaceous plants, or from the root, buds, bark, fruits, leaves or flowers in the case of woody plants.

Extracts from these plants are obtained by drying the plant material as necessary and cutting or crushing as necessary, followed by extracting into an aqueous extracting agent or organic solvent. Examples of aqueous extracting agents that can be used include cold water, warm water and hot water at the boiling point or lower temperature, while examples of organic solvents that can be used include methanol, ethanol, 1,3-butanediol and ether at normal temperature or heated.

Examples of matrix proteins in the present invention include laminin, type IV collagen, type VII collagen, parlecan and nidogen, which are constituent components of the basement membrane.

Matrix Protein Production Promoting Agent

Examples of the matrix protein production promoting agent used in the present invention include, in the case of promoting the production of these proteins, soy bean lysolecithin, transforming growth factor α (TGFa), transforming growth factor β1 (TGFb1), transforming growth factor β2 (TGFb2), transforming growth factor β3 (TGFb3) and epithelium growth factor (EGF).

In the case the artificial skin formation promoting agent or skin basement membrane stabilizing agent of the present invention contains matrix metalloproteinase inhibitor and matrix protein production promoting agent, the ratio of matrix metalloproteinase inhibitor and matrix protein production promoting agent, although varying according to their types and activity, is roughly $1:10^6$ to $10^6:1$.

Artificial Skin

Any arbitrary medium that is conventionally used for the production of artificial skin can be used for the basal medium used to produce artificial skin in the present invention, and examples of such media include Dulbecco's Modified Eagle's Medium (DMEM) containing 10% fetal calf serum, DMEM-Ham's F12 (3:1) medium containing 10% fetal calf serum, 5 μg/ml of transferrin, 5 μg/ml of insulin, 2 nM triiodotyrosine, 0.1 nM cholera toxin and 0.4 μg/ml of hydrocortisone, and keratinocyte growth medium (KGM) and DMEM containing 10% fetal calf serum mixed at a ratio of 1:1. Although varying according to the particular type, the amount of matrix metalloproteinase inhibitor added to these basal media is about 1 nmol/L to $10^{-2}$ mole/L. In addition, the amount of matrix protein production promoting agent added to the basal medium is about 1 ng/L to 1 g/L.

In the production of artificial skin of the present invention, contracted type I collagen gel containing human fibroblasts is first allowed to stand undisturbed on a metal mesh. The contracted type I collagen containing human fibroblasts can be prepared in, for example, the manner described below. After preparing a collagen solution in which fibroblasts are suspended over ice, the collagen is gelled in a Petri dish. Next, the gel is peeled from the walls of the Petri dish and the collagen gel is contracted in a $CO_2$ incubator.

Next, epidermal cells, such as normal human epidermal keratinocytes, are cultured on the above collagen gel to form epidermal. Formation of an epidermal layer by culturing epidermal cells can be carried out in the following manner. Contracted collagen gel is placed on a metal mesh, and a glass ring is placed on this gel. A suspension of epidermal keratinocytes originating in human foreskin is placed in the glass ring while preventing liquid leaking. The keratinocytes are adhered in a $CO_2$ incubator, followed by removal of the ring. The above medium is filled to the boundary of the epidermal layer and cornified layer is formed by continuing culturing while exposing the epidermal layer to the air.

According to this method, artificial skin is obtained that approximates natural skin in which an adequate basement membrane is formed between a dermal layer and epidermal layer composed of contracted type I collagen gel containing fibroblasts.

Skin Basement Membrane Formation Promoting Agent

According to the result of a study on basement membrane structural changes of facial skin for which cosmetics are primarily used that focused on a report of structural changes characterized by reduplication of the basement membrane accompanying aging as one of the changes that accompany aging (Lavker, J., Invest. Dermal. 1979, 73, 59-66), structural changes in the basement membrane begin to occur in the late twenties and have been found to accumulate with age. These structure changes of basement membrane are skin changes that precede skin changes accompanying aging, such as the formation of wrinkles, hardening or decreased resiliency.

Thus, it is essential for expression of normal skin function that epidermal basal cells be securely bound to the basement membrane, and promotion of basement membrane formation is considered to be important for this. As a result of studying wrinkle formation inhibitors using an ultraviolet radiation aged mouse model based on the presumption of routine ultraviolet rays, activity that inhibits wrinkle formation was found in drugs that are able to inhibit matrix metalloproteinase. Thus, agents that promote regeneration and repair of the basement membrane in the skin are effective as inhibitors of skin aging.

Thus, according to the present invention, a skin activating composition or basement membrane formation promoting artificial skin culturing liquid is newly provided that contains one type or a mixture of two or more types of the above matrix metalloproteinase inhibiting compound, or one type or a mixture of two or more types of this matrix metalloproteinase inhibiting compound and one type or a mixture of two or more types of a compound that demonstrates activity which increases the production of matrix protein, at a concentration sufficient for exhibiting effects that promote regeneration, repair and formation of skin basement membrane. This skin activation refers to, for example, the prevention or improvement of decreased skin function accompanying structural changes in basement membrane caused by aging and so forth, and more specifically, skin wrinkling and hardening.

The above concentration sufficient for exhibiting effects that promote regeneration, repair and formation of skin basement membrane refers may vary according to the type of compounds used, other components or vehicles used to prepare said composition, and the duration of use.

The skin basement membrane formation promoting agent of the present invention can contain active ingredient in the form of matrix metalloproteinase inhibitor, or matrix metalloproteinase inhibitor and matrix protein production promoting agent, at 0.000001 to 60 wt %, and preferably 0.00001 to 60 wt %, relative to the composition.

The skin basement membrane stabilizing agent of the present invention can be in the form of an aqueous solution, oil, other solution, milky liquid, cream, gel, suspension, microcapsules, powder, granules, capsules or solid, and after being prepared in any of these forms according to methods which are themselves known, can be coated, adhered, sprayed, injected, consumed or inserted into the body in the form of a lotion, milky liquids, cream, ointment, paste, poultice, aerosol, injection, medication (including tablets, powders, granules, pills, syrups and troaches) or suppository. Among these preparation forms, skin topical preparations such as lotions, milky liquids, creams, ointments, pastes, poultices and aerosols are considered to be preparation forms that are suitable for the composition of the present invention. The skin topical preparations described here include prescription drugs, non-prescription drugs and cosmetics, and are to be used with the same meaning hereinafter.

Vehicles and fragrances routinely used when preparing such compositions, as well as oils, surfactants, antiseptics, sequestering agents, water-soluble polymers, thickeners, powder ingredients, ultraviolet defensive agents, moisturizing agents, pharmacologically effective ingredients, antioxidants, pH adjusters, cleaning agents, drying agents, emulsifiers and so forth can be suitably blended into the composition of the present invention. In the case of blending each of these ingredients into the skin activating composition of the present invention, it is necessary to blend them within a range that does not impair the desired effect of the present invention.

Examples of the above oil include liquid oils, solid oils, waxes, hydrocarbon oils, higher fatty acids, higher alcohols, synthetic ester oils and silicones.

More specifically, examples of liquid oils include avocado oil, tsubaki oil, primrose oil, turtle oil, *macadamia* nut oil, corn oil, mink oil, olive oil, rape seed oil, egg yolk oil, sesame oil, persic oil, wheat germ oil, sasanqua oil, castor oil, linseed oil, safflower oil, cottonseed oil, perilla oil, soy bean oil, peanut oil, theine oil, kaya oil, rice bran oil, Chinese wood oil, Japanese wood oil, hohoba oil, germ oil, triglycerin, trioctanoic glycerin and triisopalmitic glycerin; examples of solid oils include cacao butter, coconut oil, horse tallow, hardened coconut oil, palm oil, beef tallow, goat tallow, hardened beef tallow, palm heart oil, pork tallow, beef bone tallow, haze heart oil, hardened oil, beef leg tallow, haze wax and hardened castor oil; examples of waxes include beeswax, candelilla wax, cotton wax, carnauba wax, bayberry wax, tree wax, spermaceti, montan wax, bran wax, lanolin, kapok wax, lanolin acetate, liquid lanolin, sugar cane wax, isopropyl lanolin fatty acid, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol and POE hydrogenated lanolin alcohol ether; and examples of hydrocarbon oils include liquid paraffin, ozokerite, squalane, pristan, paraffin, ceresin, squalene, VASELINE™ (petroleum jelly) and microcrystalline wax.

Examples of higher fatty acids include lauric acid, myristic acid, palmitic acid, stearic acid, behenic (beheninic) acid, oleic acid, 12-hydroxystearic acid, undecylenic acid, tolic acid, isostearic acid, linoleic acid, linolenic acid, eicosapentanoic acid (EPA) and docosahexanoic acid (DHA).

Examples of higher alcohols include lauryl alcohol, cetyl alcohol, stearyl alcohol, behenyl alcohol, myristyl alcohol, oleyl alcohol, cetostearyl alcohol and other straight chain alcohols, as well as monostearyl glycerin ether (vatyl alcohol), 2-decyltetradecinol, lanolin alcohol, cholesterol, phytosterol, hexyldodecanol, isostearyl alcohol, octyldecanol and other branched chain alcohols.

Examples of synthetic ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, n-alkylglyol monoisostearate, glycerin di-2-heptylundecanoate, trimethylolpropane tri-2-ethylhexylate, trimethylolpropane triisostearate, pentaneerythritol tetra-2-ethylhexylate, glycerin tri-2-ethylhexylate, trimethylolpropane triisostearate, cetyl-2-ethyl hexanoate, 2-ethylhexyl palmitate, glycerin trimyristate, tri-2-heptylundecanoic glyceride, castor oil fatty acid methyl ester, oleic oil, cetostearyl alcohol, acetoglyceride, 2-heptylundecyl palmitate, diisobutyl adipate, N-lauroyl-L-glutamate-2-octyldodecyl ester, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate and triethyl citrate.

Examples of silicones include dimethyl polysiloxane, methylphenyl polysiloxane, methylhydrogen polysiloxane and other linear polysiloxanes, decamethyl polysiloxane, dodecamethyl polysiloxane, tetramethyltetrahydrogen polysiloxane and other cyclic polysiloxanes, and silicon resin and silicone rubber that form a three-dimensional mesh structure.

The skin basement membrane stabilizing agent of the present invention may contain anionic surfactant, cationic surfactant, amphoteric surfactant or nonionic surfactant and so forth either alone or in combination.

Examples of anionic surfactants include fatty acid soaps such as soap base, sodium laurate and sodium palmitate; higher alkyl sulfate esters such as sodium lauryl sulfate and potassium lauryl sulfate; alkyl ether sulfate ester salts such as POE triethanol amine lauryl sulfate and POE sodium lauryl sulfate; N-acylsarcosinic acids such as sodium lauroylsarcosine; higher fatty acid amide sulfonates such as sodium N-myristoyl-N-taurine, sodium coconut oil fatty acid methyltauride and sodium laurylmethyltauride; phosphate esters such as POE sodium oleyl ether phosphate and POE stearyl ether phosphate; sulfosuccinates such as sodium di-2-ethylhexylsulfosuccinate, sodium monolauroylmonoethanolamide polyoxyethylene sulfosuccinate and sodium laurylpolypropylene glycol sulfosuccinate; alkylbenzene sulfonates such as linear sodium dodecylbenzene sulfonate, linear dodecylbenzene sulfonate triethanolamine and linear dodecylbenzene sulfonate; N-acylglutamates such as monosodium N-lauroylglutamate, disodium N-stearoylglutamate and monosodium N-myristoyl-L-glutamate; higher fatty acid ester sulfate esters such as sodium hardened coconut oil fatty acid glycerin sulfate; sulfated oils such as Turkey red oil oil; as well as POE alkyl ether carboxylic acid, POE alkylaryl ether carboxylic acid, α-olefin sulfonate, higher fatty acid ester sulfonate, secondary alcohol sulfate ester, higher fatty acid alkylolamide sulfate ester, sodium lauroylmonoethanolamide succinate, N-palmitoylaspartate ditriethanolamine and sodium casein.

Examples of cationic surfactants include alkyl trimethyl ammonium salts such as stearyl trimethyl ammonium chloride and lauryl trimethyl ammonium chloride, dialkyl dimethyl ammonium salts such as distearyl dimethyl ammonium chloride, alkyl pyridinium salts such as (N,N'-dimethyl-3,5-methylene piperidinium) chloride and cetyl pyridinium chloride, alkyl quaternary ammonium salts, alkyl dimethylbenzyl ammonium salts, alkyl isoquinolinium salts, dialkyl morpholinium salts, POE alkyl amines, alkyl amine salts, polyamine fatty acid derivatives, amyl alcohol fatty acid derivatives, benzalkonium chloride and benzetonium chloride.

Examples of amphoteric surfactants include imidazoline-based amphoteric surfactants such as 2-undecyl-N,N,N-(hydroxyethylcarboxymethyl)-2-imidazoline sodium and 2-cocoyl-2-imidazolinium hydroxide-1-carboxyethyloxy-2-sodium salt, and betaine-based amphoteric surfactants such as 2-heptadecyl-N-carboxymethyl-N-hydroxyethylimidazolinium betaine, lauryldimethylaminoacetate betaine, alkyl betaine, amidobetaine and sulfobetaine.

Examples of lipophilic nonionic surfactants include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, penta-2-ethylhexylic diglycerol sorbitan and tetra-2-ethylhexylic diglycerol sorbitan, glycerin polyglycerin fatty acids such as glycerin mono-cottonseed oil fatty acid, glycerin monoerucate, glycerin sesquiolate, glycerin monostearate, glycerin α,α'-oleic pyroglutamate, glycerin monostearate and malic acid, propylene glycol fatty acid esters such as propylene glycol monostearate, hardened castor oil derivatives, glycerin alkyl ether and polyoxyethylene-methylpolysiloxane copolymers.

Examples of hydrophilic nonionic surfactants include POE sorbitan fatty acid esters such as POE sorbitan monooleate, POE sorbitan monostearate, POE sorbitan monooleate and POE sorbitan tetraoleate, POE sorbitol fatty acid esters such as POE sorbitol monolaurate, POE sorbitol monooleate, POE sorbitol pentaoleate and POE sorbitol monostearate, POE glycerin fatty acid esters such as POE glycerin monostearate, POE glycerin monoisostearate and POE glycerin triisostearate, POE fatty acid esters such as POE monooleate, POE distearate, POE monodioleate and ethylene glycol distearate, POE alkyl ethers such as POE lauryl ether, POE oleyl ether, POL stearyl ether, POE behenyl ether, POE 2-octyldodecyl ether and POE cholestanol ether, POE alkylphenyl ethers such as POE octylphenyl ether, POE nonylphenyl ether and POE dinonylphenyl ether, plurallonics such as pluronic, POE-POP alkyl ethers such as POE-POP cetyl ether, POE-POP 2-decyltetradecyl ether, POE-POP monobutyl ether, POE-POP hydrogenated lanolin and POE-POP glycerin ether, tetra POE-tetra POP ethylene diamine condensation products such as tetronic, POE castor oil/hardened castor oil derivatives such as POE castor oil, POE hardened castor oil, POE hardened castor oil monoisostearate, POE hardened castor oil triisostearate, POE hardened castor oil monopyroglutamate monoisostearate diester and POE hardened castor oil maleate, POE beeswax-lanolin derivatives such as POE sorbitol beeswax, alkanol amides such as coconut oil fatty acid diethanol amide, lauric monoethanol amide and fatty acid isopropanol amide, POE propylene glycol fatty acid esters, POE alkyl amines, POE fatty acid amides, sucrose fatty acid esters, POE nonylphenyl formaldehyde compounds, alkylethoxydimethyl amine oxides and trioleyl phosphates.

Examples of the above-preservatives include methyl parabenzene, ethyl parabenzene and butyl parabenzene.

Examples of the above sequestering agents include sodium edetate and EDTA.

Examples of the above water-soluble polymers include natural polymers, semi-synthetic polymers, synthetic polymers and inorganic polymers.

Examples of natural water-soluble polymers include plant polymers such as gum arabic, tragacanth gum, galactan, guar gum, carob gum, karaya gum, carageenan, tamarind gum, xanthane gum, pectin, agar, queenseed marmelo, algea colloid (brown algae extract), starch (rice, corn, potato, wheat) and glycyrrhizic acid, microbial polymers such as xanthane gum, dextran succinoglucan and pluran, and animal polymers such as collagen, casein, albumin and gelatin.

Examples of semi-synthetic water-soluble polymers include starch-based polymers such as dextrin, carboxymethyl starch and methylhydroxypropyl starch, cellulose-based polymers such as methyl cellulose, nitrocellulose, ethyl cellulose, methylhydroxypropyl cellulose, hydroxyethyl cellulose, cellulose dimethyl dialkyl (12-20) ammonium sulfate, hydroxypropyl cellulose, sodium carboxymethyl cellulose (CMC), crystalline cellulose and powdered cellulose, alginate-based polymers such as sodium alginate and propylene glycol alginate ester.

Examples of synthetic water-soluble polymers include vinyl-based polymers such as polyvinyl alcohol, polyvinyl methyl ether, polyvinyl pyrrolidone, carboxyvinyl polymer and alkyl denatured carboxyvinyl polymer, polyoxyethylene-based polymers such as polyethylene glycol 2000, 4000 and 6000, polyoxyethylene polyoxypropylene copolymer-based polymers, acrylic polymers such as sodium polyacrylate, polyethylene acrylate and polyacrylamide, polyethylene imines and cationic polymers.

Examples of inorganic water-soluble polymers include bentonite, magnesium aluminum silicate, raponite, hectrite and silicic anhydride.

Examples of the above powder component include inorganic powders such as talc, kaolin, mica, sericite, muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal tungstate, magnesium silica, zeolite, barium sulfate, baked calcium sulfate (baked gypsum), calcium phosphate, fluoroapatite, hydroxyapatite, ceramic powder, metal soap (zinc myristate, calcium palmitate, aluminum stearate) and boron nitride, organic powders such as polyamide resin powder (Nylon powder), polyethylene powder, polymethyl methacrylate powder, polystyrene powder, styrene and acrylic acid copolymer resin powder, benzoguanamine resin powder, polytetrafluoroethylene powder and cellulose powder, inorganic white pigments such as titanium dioxide and zinc oxide, inorganic red pigments such as iron oxide (rouge) and iron titanate, inorganic brown pigments such as γ-iron oxide, inorganic yellow pigments such as yellow iron oxide and ocher, inorganic black pigments such as black iron oxide, carbon black and low order titanium oxide, inorganic violet pigments such as mango violet and cobalt violet, inorganic green pigments such as chromium oxide, chromium hydroxide and cobalt titanate, inorganic blue pigments such as ultramarine and Prussian blue, pearl pigments such as titanium oxide coated mica, titanium oxide coated bismuth oxychloride, titanium oxide coated talc, colored titanium oxide coated mica, bismuth oxychloride and fish scale foil, metal powder pigments such as aluminum powder and copper powder, zirconium, barium or aluminum lake organic pigments such as red no. 201, red no. 202, red no. 204, red no. 205, red no. 220, red no. 226, red no. 228, red no. 405, orange no. 203, orange no. 204, yellow no. 205, yellow no. 401, yellow no. 404, red no. 3, red no. 104, red no. 106, red no. 227, red no. 230, red no. 401, red no. 505, orange no. 205, yellow no. 4, yellow no. 5, yellow no. 202, yellow no. 203, green no. 3 and blue no. 1, natural pigments such as chlorophyll and β-carotene, and colorants such as titanium yellow, carsamine and saffron red.

Examples of the above ultraviolet defensive agents include both "ultraviolet absorbers", which are substances that chemically absorb ultraviolet rays, and "ultraviolet blockers", which are substances that scatter and reflect ultraviolet rays by physical action.

Namely, examples of long-wavelength ultraviolet (UVA) absorbers include anthranilic acid-based ultraviolet absorbers such as methyl anthranilate and homomethyl-N-acetylanthranilate, benzophenone-based ultraviolet absorbers such as 2,4-dihydroxybenzophenone, 2,2-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid, 4-phenylbenzophenone, 2-ethylhexyl-4'-phenyl-benzophenone-2-carboxylate, 2-hydroxy-4-n-octoxybenzophenone and 4-hydroxy-3-carboxybenzophenone, benzotriazole-based ultraviolet absorbers such as 2,2'-hydroxy-5-methylphenylbenzotriazole, 2-(2'-hydroxy-5'-t-octylphenyl)benzotriazole and 2-(2'-hydroxy-5'-methylphenyl)benzotriazole, dianisoylmethane and 4-methoxy-4'-t-butyldibenzoylmethane.

Among these long-wavelength ultraviolet absorbers, 4-methoxy-4'-tert-butyldibenzoylmethane, 2-hydroxy-4-methoxybenzophenone and 2-hydroxy-4-methoxybenzophenone derivatives such as 2-hydroxy-4-methoxybenzophenone-5-sulfonate are preferable because they are long-wavelength ultraviolet absorbers having superior safety and effectiveness.

In addition, examples of medium-wavelength ultraviolet (UVB) absorbers include benzoic acid-based ultraviolet absorbers such as paraminobenzoic acid (to be abbreviated as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester and N,N-dimethyl PABA amyl ester, salicylic acid-based ultraviolet absorbers such as dipropylene glycol salicylate, ethylene glycol salicylate, myristyl salicylate, methyl salicylate, amyl salicylate, menthyl salicylate, homomethyl salicylate, octyl salicylate, phenyl salicylate, benzyl salicylate and p-isopropanol phenyl salicylate, cinnamic acid-based ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxymethyl-p-methoxycinnamate, cyclohexyl-p-methoxycinnamate, ethyl-α-cyano-β-phenylcinnamate, 2-ethylhexyl-α-cyano-β-phenylcinnamate, glycerylmono-2-ethylhexanoyl-diparamethoxycinnamate, methoxycinnamate octyl, 3,4,5-trimethoxycinnamate-3-methyl-4-[methylbis (trimethylsiloxy)silyl]butyl and p-dimethoxycinnamate monoethyl ester, camphor derivatives such as 3-(4'-methylbenzylidene)-d,1-camphor, 3-benzylidene-d,1-camphor and 5-(3,3-dimethyl-2-norvolnilidene)-3-penten-2-one, urocanic acid, urocanic ethyl ester, 2-phenyl-5-methylbenzooxazole and dibenzaladine.

Moreover, examples of ultraviolet blockers include titanium oxide ($TiO_2$), talc ($MgSiO_2$), carmine ($FeO_2$), bentonite, kaolin and zinc oxide (Zno).

Examples of the above moisturizing agents include polyethylene glycol, propylene glycol, glycerin, 1,3-butylene glycol, hexylene glycol, xylitol, sorbitol, maltitol, chondroitin sulfuric acid, hyaluronic acid, mucoitin sulfuric acid, charoninic acid, atherocollagen, cholesteryl-12-hydroxystearate, sodium lactate, bile acid salt, dl-pyrrolidone carboxylate, short chain soluble collagen, diglycerin (EO) PO addition product, Chestnut rose Fruit extract, milfoil extract and melilote extract.

Examples of the above pharmacologically effective ingredients include whiteners such as albutin, vitamin C and its derivatives, kojic acid placental extract, glutathione and saxifrage extract, antiphlogistics such as glycyrrhizic acid derivatives, glycyrrhetinic acid derivatives, salicylic acid derivatives, hinokitiol, zinc oxide and allantoin, activators such as royal jelly, actinolite, cholesterol derivatives and calf blood extract, circulation promoters such as nonylic urenylamide, nicotinic benzyl ester, nicotinic β-butoxyethyl ester, capsisin, zingerone, cantharidin, ichthammol, caffeine, tannic acid, α-borneol, nicotinic tocopherol, inositol hexanicotinate, cyclandelate, cinnarizine, tolazoline, acetylcholine, verapamil, cepharanthin and γ-olizanol, antiseborrheics such as sulfur and thianthol, and for various purposes, Phellodendron Bark extract component, goldthread extract component, Lithospermum Root extract component, peony extract component, gentian extract component, birch extract component, sage extract component, loquat extract component, carrot extract component, aloe extract component, mallow extract component, iris extract component, grape extract component, Coix Seed extract component, sponge cucumber extract component, lily extract component, saffron extract component, Cnidium Officinale Root extract component, Ginger Root extract component, Saint John's-wort extract component, Restharrow Root extract component, rosemary extract component, garlic extract component, red pepper extract component, dried orange peel, Japanese angelica root and so forth, vitamin A substances such as retinol and retinol acetate, vitamin $B_2$ substances such as riboflavin butyrate and riboflavin adenine nucleotide, vitamin B2 substances such as pyridoxine hydrochloride and pyridoxine dioctanoate, vitamin C substances such as L-ascorbic acid, L-ascorbate dipalmitate ester, L-ascorbate-2-sodium sulfate, L-ascorbate phosphate ester and dipotassium DL-α-tocopherol-L-ascorbate phosphate diester, pantothenic acids such as calcium pantothenate, D-pantothenyl alcohol, pantothenyl ethyl ether and acetylpentothenyl ethyl ether, vitamin D substances such as ergocalciferol and cholecalciferol, nicotinic acids such as nicotinic acid, nicotinic amide and benzyl nicotinate, vitamin E substances such as α-tocopherol and DL-α-tocopherol succinate, and other vitamins such as vitamin P and biotin.

Furthermore, these pharmacological components can be widely blended within a range over which the desired pharmacological effect of the present invention is not impaired by that blending.

The composition of the present invention prepared in this manner prevents decreased function accompanying structural changes of basement membrane, and promotes activation of the skin.

EXAMPLES

The following provides a more detailed explanation of the present invention through its examples.

Example 1

Production of Artificial Skin Using Matrix Metalloproteinase Inhibitor

Collagen gel was obtained by preparing 10 ml of a collagen solution of suspended fibroblasts (0.3 to $1\times10^5$ cells/ml) originating in human dermis (product I-AC of Koken Co., Ltd. was used for the collagen) on ice followed by gelling the collagen at 37° C. in a 60 mm Petri dish. Next, the gel was peeled from the walls of the Petri dish and the collagen gel was contracted in a $CO_2$ incubator.

This contracted collagen gel equivalent to dermis was placed on a metal mesh and a glass ring (inner diameter: 12 mm) was placed over this gel. 0.4 ml of a suspension of epidermal keratinocytes ($1\times10^6$/ml) (mixed medium of KGM-DMEM containing 5% fetal calf serum (1:1)) were placed inside the glass ring to prevent leakage of liquid. After adhering keratinocytes in a $CO_2$ incubator overnight, the ring was removed on the following day. The above medium was filled to the boundary of the epidermal layer and culturing was continued while exposing the epidermal layer to air to produce a skin model having a stratified epidermis exhibiting corneal layer formation.

After inoculating the epidermic cells, the medium was changed to that containing either (1) 10 µM CGS27023A (matrix metalloproteinase inhibitor) or (2) 300 µM MMP-inhibitor (p-$NH_2$-Bz-Gly-Pro-D-Leu-D-Ala-NHOH (FN-437) (BBRC, 1994, 199, p. 1442-1446) (acquired from Cabbiochem. Novabiochem Corporation) (matrix metalloproteinase inhibitor)) starting in the first week, and then replaced with medium containing the same type and same concentration of matrix metalloproteinase inhibitor every 2-3 days after that and cultured for 2 weeks. In addition, (3) similar culturing was carried out without adding matrix metalloproteinase inhibitor for use as a control.

Figure 1:
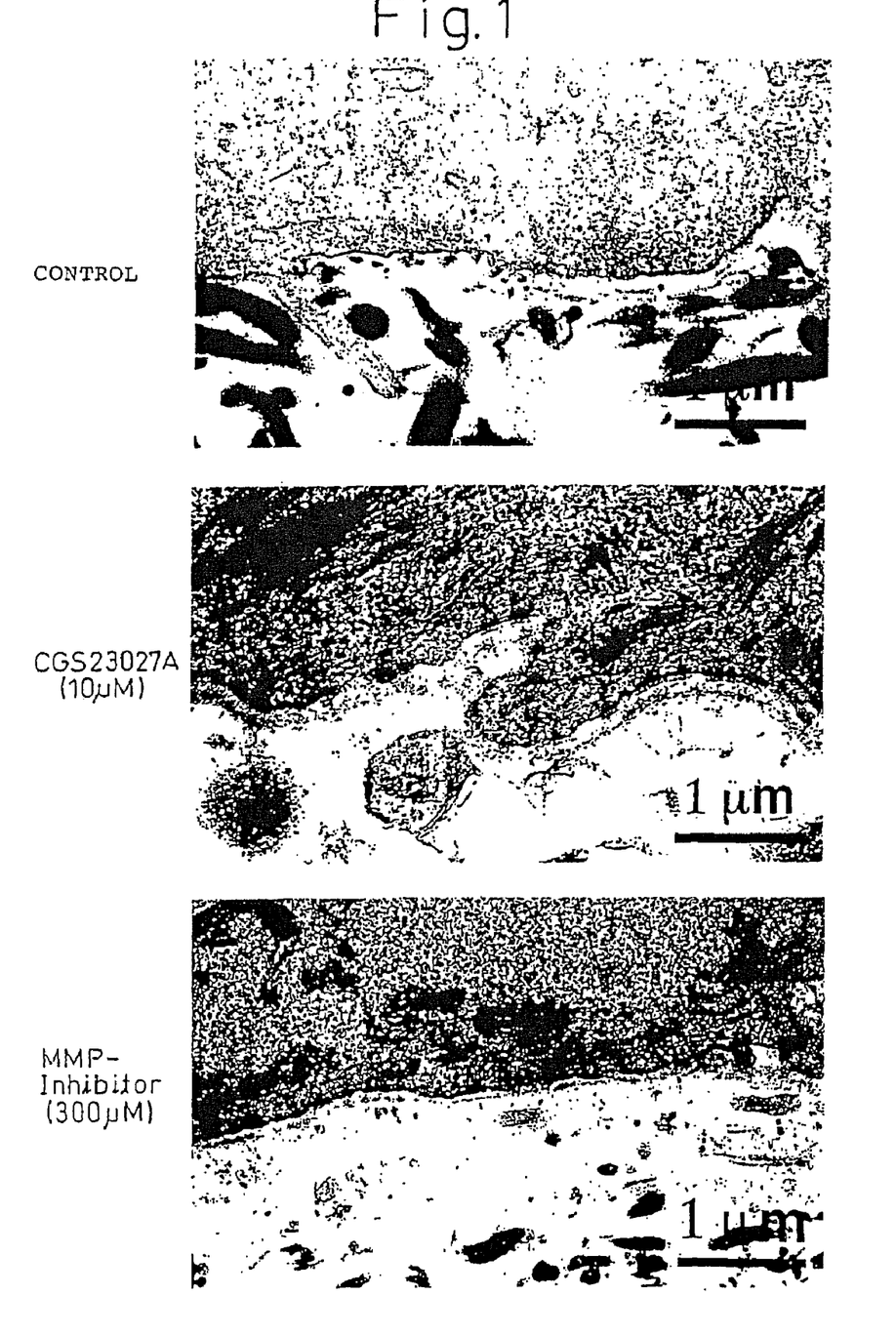
FIG. 1 is a photograph representing a biological form of the cross-section of artificial skin comparing the case of addition of matrix metalloproteinase CGS27023A (10 μM) or MMP inhibitor (300 μM) with a control to which neither is added in culturing for the formation of artificial skin.

Those results are shown in FIG. 1. As is clear from the figure, although a basement membrane-like structure was not observed directly beneath the basal cells of the epidermis in control (3), in the case of adding matrix metalloproteinase inhibitors (1) CGS27023A compound or (2) MMP-inhibitor, promotion of basement membrane formation was clearly observed.

A similar experiment was carried out for extracts of the plants indicated below instead of the above matrix metalloproteinase inhibitor compounds to confirm promotion of basement membrane formation.

Similar effects were confirmed for *Thymus serpyllum* L., *Valeriana fauriei* Briquet or other similar plants (Valerianaceae), *Diospyros kaki* Thunberg (Ebenaceae), *Astragalus sinicus* Linne (Leguminosae), *Crataegus cuneata* Siebold et Zuccarini (Rosaceae), *Paeonia suffruticosa* Andrews (*Poeonia montan* Sims) (Paconiaceae), *Thea sinensis* Linne var. *assamica* Pierre (Thcaccae), *Eucalyptus globulus* Labillardiere or its similar plants (Myrtaceae), *Potentilla tormentilla* Schrk (Rosaceae), *Tilia corda*:a Mill., *Tilia platyphyllus* Scop., *Tilia europaea* Linne (Tiliaceae), *Betula alba* Linne (Betulaceze), *Origanum majorana* L., *Uncaria gambir* Roxburgh (Rubiaceae), *Juglans regia* Linne var. *sinensis* De Candolie or its similar plants (Juglandaceae), *Sophora flavescens* Aiton (Leguminosae), *Sanguisorba officinalis* Linne (Rosaceae), *Hypericum perforatum* Linne or *Hypericum erectum* Thunberg (Guttiferae), *Thea sinensis* Linne (Theaceae), *Curcuma longa* L (Zingiberaceae), purified extracts of *Curcuma longa* L including *Symplocos racemosa* and *Cyperus rotundus*, *Cyperpus scariosus*, *Gaultheria fragrantissima*, *Acacia* formensia, *Terminalia chebula*, *Ficus bengalensis*, *Cassia fistula* Linn, *Lyonia ovalifolia*, *Calophyllum inophyllum* and *Ficus religiosa*.

Example 2

Production of Artificial Skin Using Both Matrix Metalloproteinase Inhibitor and Matrix Protein Production Promoting Agent Although the same method as Example 1 was repeated, the following substances were used as test substances.
(1) 10 μM matrix metalloproteinase inhibitor CGS27023A only;
(2) 10 μM matrix metalloproteinase inhibitor CGS27023A and 10 ng/ml of matrix metalloproteinase protein production promoting agent, Transforming Growth Factor α (TGFa);
(3) 10 μM matrix metalloproteinase inhibitor CGS27023A and 10 ng/ml of matrix protein production promoting agent, Transforming Growth Factor β1 (TGFb1);
(4) 10 μM matrix metalloproteinase inhibitor CGS27023A, 10 ng/ml of matrix protein production promoting agent, Transforming Growth Factor α (TGFa) and 10 ng/ml of Transforming Growth Factor β1 (TGFb1); and
(5) culturing of a control to which none of the above were added.

Figure 2:
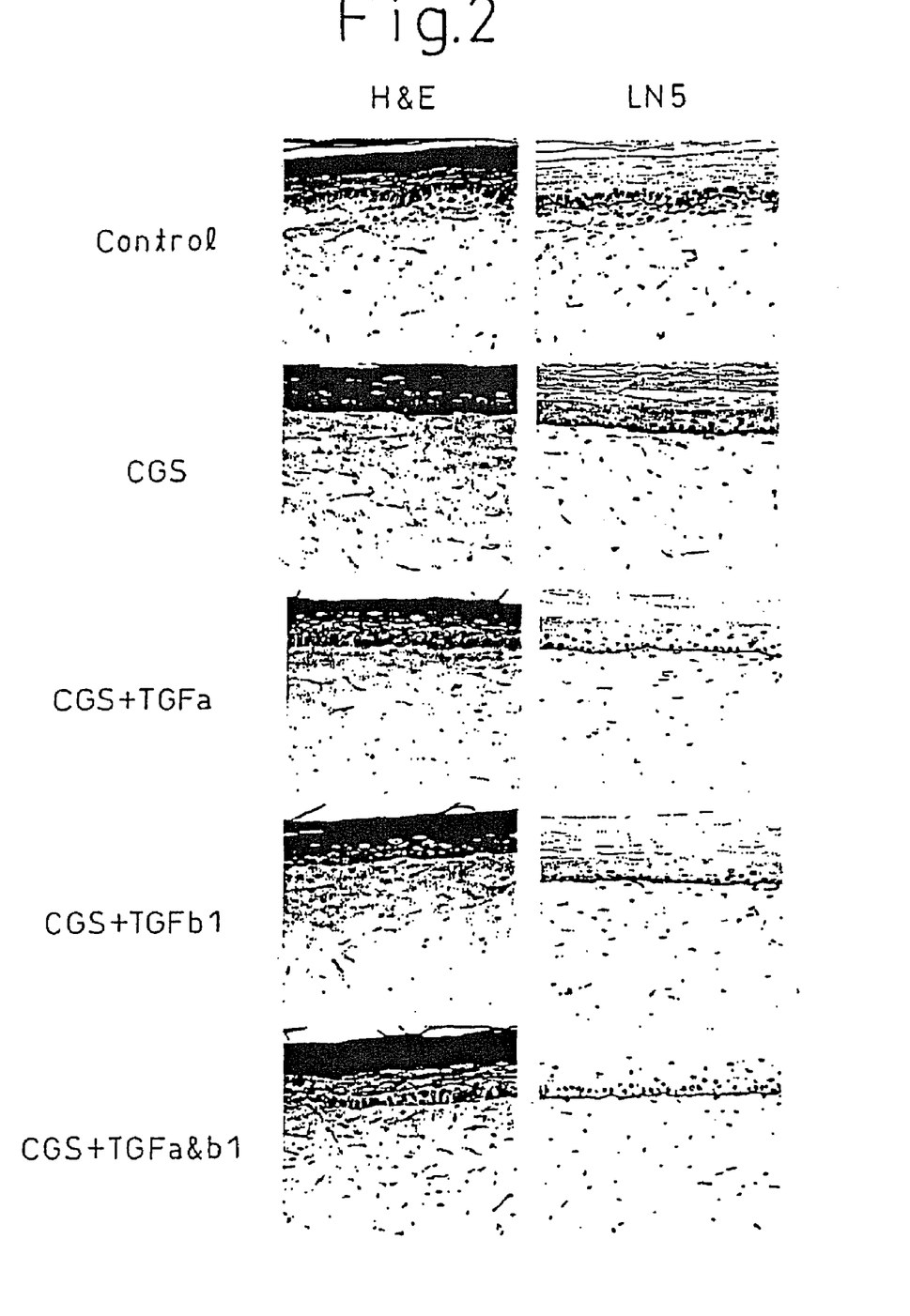
FIG. 2 is a photograph representing a biological form of the cross-section of artificial skin that shows the results of performing hematoxylin and eosin staining (H & E) and immunostaining (detection of laminin (LN5)) on formed artificial skin in the case of adding matrix metalloproteinase inhibitor CGS27023A (shown as CGS) only, the case of adding CGS and transforming growth factor α, a matrix protein production promoting agent (CGS+TGFa), the case of adding CGS and transforming growth factor β1, a matrix protein production promoting agent (CGS+TGFb1), and the case of adding both TGFa and TGFb1 to CGS (CGS+TGFa+TGFb1) to the medium during culturing for formation of artificial skin.
Figure 3:
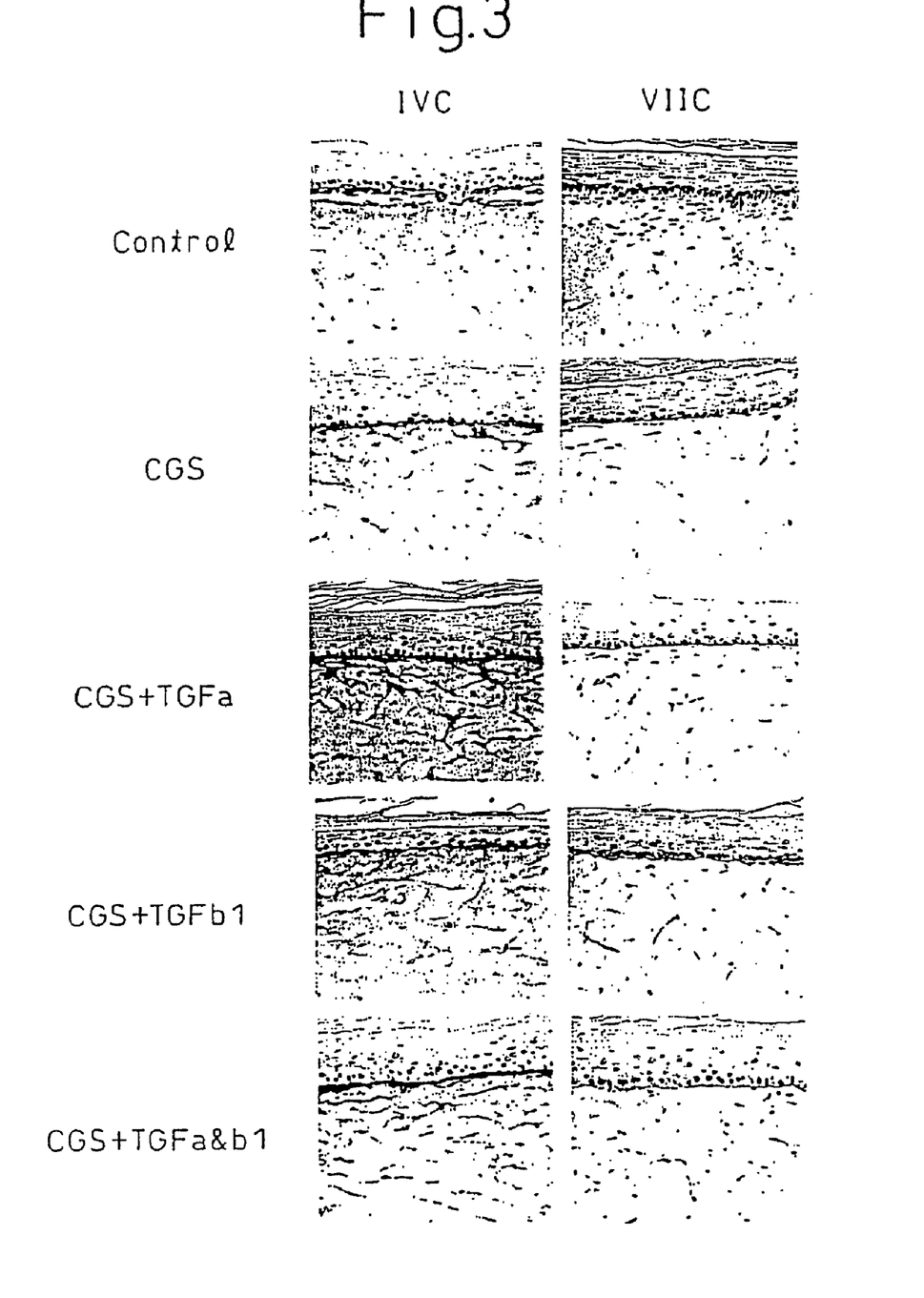
FIG. 3 is a photograph used in place of a drawing representing a biological form of a fragment of artificial skin showing the results of performing immunostaining (detection of type IV collagen (IVC) and detection of type VII collagen (VIIC)) in the same experiment as FIG. 2.

The formed artificial skin was stained by hematoxylin-eosin (H & E) and immunostaining (using anti-laminin 5 (LN5) antibody, anti-type IV collagen (IVC) antibody, and anti-type VII collagen (VIIC) antibody). Those results are shown in FIG. 2, FIG. 3 and Table 1. Furthermore, the results for H & E and LN5 are shown in FIG. 2, while the results for IVC and VIIC are shown in FIG. 3.

In the control, adhesion of epidermis/dermis joined portions was weak, the epidermis easily peeled from the dermis and there were voids observed in the tissue. In contrast, in the group treated with matrix metalloproteinase inhibitor CGS27023A, adhesion between the epidermis and dermis was clear. In addition, in the case of adding matrix protein production promoting agent, Transforming Growth Factor α (TGFa), Transforming Growth Factor β1 (TGFb1) or both (TGFa+TGFb1) in addition to matrix metalloproteinase inhibitor CGS27023A, staining of type VII collagen in particular was promoted significantly, thereby confirming that adhesion between the epidermis and dermis was further promoted.

TABLE 1

Effects of Various Drugs on Basement Membrane Formation in a Skin Model

| Treatment conditions | Deposition of basement membrane component | | | |
| --- | --- | --- | --- | --- |
|  | Laminin 5 | Type IV collagen | Type VII collagen | Basement membrane formation |
| Non-treatment control group | + | + | − | − |
| CGS27023A | ++ | ++ | + | + |
| CGS27023A + soybean lecithin | ++ | ++ | ++ | ++ |
| CGS27023A + TGFα | ++ | ++ | ++ |  |
| CGS27023A + TGFβ1 | ++ | ++ | ++ |  |
| CGS27023A + TGFα + TGFβ1 | ++ | ++ | ++ |  |

Culturing was carried out in the same manner as above using the following plant extracts instead of the above matrix metalloproteinase inhibitor CGS27023A.

*Thymus serpyllum* L., *Valeriana fauriei* Briquet or other similar plants (Valerianaceae), *Diospyros kaki* Thunberg (Ebenaceae), *Astragalus sinicus* Linne (Leguminosae), *Crataegus cuneata* Siebold et Zuccarini (Rosaceae), *Paeonia suffruticosa* Andrews (*Poeonia montan* Sims) (Paconiaceae), *Thea sinensis* Linne var. *assamica* Pierre (Thcaccae), *Eucalyptus globulus* Labillardiere or its similar plants (Myrtaceae), *Potentilla tormentilla* Schrk (Rosaceae), *Tilia corda*:a Mill., *Tilia platyphyllus* Scop., *Tilia europaea* Linne (Tiliaceae), *Betula alba* Linne (Betulaceze), *Origanum majorana* L., *Uncaria gambir* Roxburgh (Rubiaceae), *Juglans regia* Linne var. *sinensis* De Candolie or its similar plants (Juglandaceae), *Sophora flavescens* Aiton (Leguminosae), *Sanguisorba officinalis* Linne (Rosaceae), *Hypericum perforatum* Linne or *Hypericum erectum* Thunberg (Guttiferae), *Thea sinensis* Linne (Theaceae), *Curcurna longa* L (Zingiberaceae), purified extracts of *Curcuma longa* L including *Symplocos racemosa* and *Cyperus rotundus*, *Cyperus scariosus*, *Gaultheria fragrantissima*, *Acacia formensia*, *Terminalia chebula*, *Ficus bengalensis*, *Cassia fistula* Linn, *Lyonia ovalifolia*, *Calophyllum inophyllum* and *Ficus religiosa*.

As a result, results were obtained that were similar to the case of using CGS27023A as matrix metalloproteinase inhibitor. In addition, similar results were also obtained for *Symplocos racemosa*, a purified extract of *Curcuma longa* L.

Figure 4:
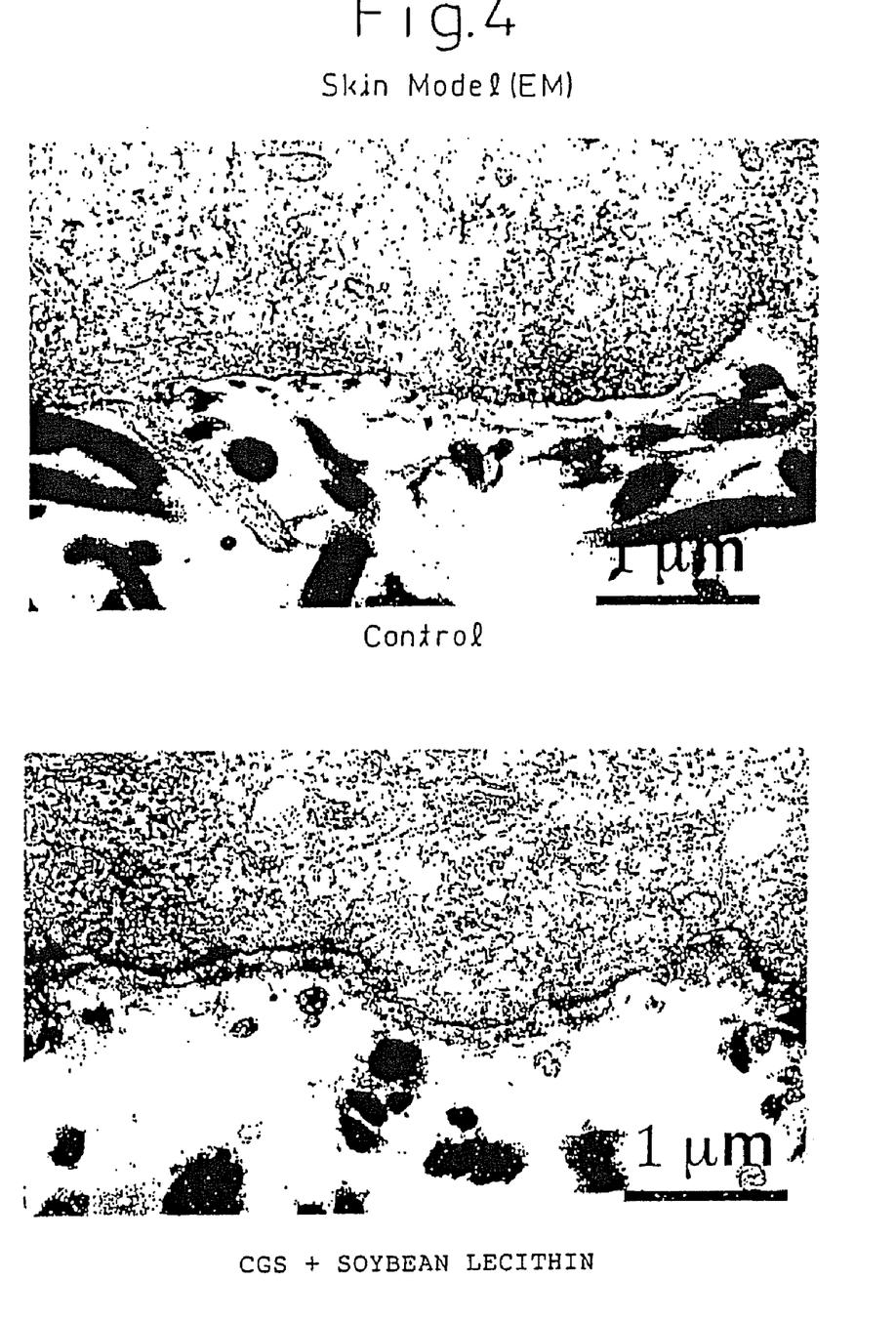
FIG. 4 is a photograph representing a biological form of cross-sections of artificial skin formed in the case of adding matrix metalloproteinase inhibitor CGS27023A and soy bean lecithin, a matrix protein production promoting agent (CGS+ soy bean lecithin), and the case of not adding the above substances (control) to the medium during culturing for the formation of artificial skin.

Moreover, a structure resembling a basement membrane was continuously observed directly beneath the basal cells in the case of using 30 μg/ml of soy bean lecithin instead of Transforming Growth Factor for the matrix protein production promoting agent. Those results are shown in FIG. 4.

Example 3

Preparation of Artificial Skin Culture Medium

Matrix metalloproteinase inhibitor CGS27023A or MMP-inhibitor were added to a concentration of 10 μM to basal medium comprising a 1:1 mixture of KGM (keratinocyte growth medium), typically used to culture epidermic cells, and Dulbecco's Modified Eagle's Medium containing 10% fetal calf serum, typically used to culture fibroblasts. Furthermore, KGM was prepared by adding HEPES (6.7 g/L), NaHCO$_3$ (1.2 g/L), insulin (5 mg/L), transferrin (10 mg/L), hydrocortisone (0.5 mg/L) and phosphorylethanolamine (14.1 mg/L) to MCDB153 medium (10.93 g/L) and adjusting the pH to 7.4 followed by the addition of 20 g of bovine pituitary extract (Far East Pharmaceutical).

Example 4

Preparation of Artificial Skin Culture Medium

At least one type of Transforming Growth Factor α (TGFa) or Transforming Growth Factor β1 (TGFb1) were added as matrix protein production promoting agent to the artificial skin culture medium in Example 3 to a concentration of 10 ng/ml.

In addition, soy bean lecithin was added at 30 μg/ml in place of the above TGFa or TGFb1.

| Preparation Example 1: Cream | |
|---|---|
| Polyoxyethylene (addition of 20 moles) cetyl alcohol ether | 1.0 |
| Methylphenyl polysiloxane (20 cs) | 2.0 |
| Liquid paraffin | 3.0 |
| 2-hydroxy-4-methoxybenzophenone | 5.0 |
| Active ingredient | 0.2 |
| Propylene glycol | 5.0 |
| Glycerin | 2.0 |
| Ethyl alcohol | 15.0 |
| Carboxyvinyl polymer | 0.3 |
| Hydroxypropyl cellulose | 0.1 |
| 2-aminomethylpropanol | 0.1 |
| Antiseptic | As suitable |
| Fragrance | As suitable |
| Ion exchanged water | As suitable |

(Production Method)

Propylene glycol, glycerin, ethyl alcohol, carboxyvinyl polymer, hydroxypropyl cellulose and 2-aminomethylpropanol were added to ion exchanged water followed by heating to 70° C. (aqueous phase).

Methylphenyl polysiloxane, liquid paraffin, polyoxyethylene cetyl alcohol ether, antiseptic, 2-hydroxy-4-methoxybenzophenone, active ingredient (such as lipidure and/or CGS27023A) and fragrance were mixed and prepared to 70° C. (oily phase).

After gradually adding the aqueous phase to the oily phase, pre-emulsifying and obtaining homogeneous emulsified particles using a homomixer, the emulsion was deaerated and cooled to obtain a cream.

| Preparation Example 2: Cream | |
|---|---|
| Polyoxyethylene (addition of 20 moles) cetyl alcohol ether | 1.0 |
| Methylphenyl polysiloxane (20 cs) | 2.0 |
| Liquid paraffin | 3.0 |
| 2-hydroxy-4-methoxybenzophenone | 5.0 |
| Active ingredient | 0.2 |
| Propylene glycol | 5.0 |
| Glycerin | 2.0 |
| Ethyl alcohol | 15.0 |
| Carboxyvinyl polymer | 0.3 |
| Hydroxypropyl cellulose | 0.1 |
| 2-aminomethylpropanol | 0.1 |
| Antiseptic | As suitable |
| Fragrance | As suitable |
| Ion exchanged water | As suitable |

(Production Method)

Propylene glycol, glycerin, ethyl alcohol, carboxyvinyl polymer, hydroxypropyl cellulose and 2-aminomethylpropanol were added to ion exchanged water followed by heating to 70° C. (aqueous phase).

Methylphenyl polysiloxane, liquid paraffin, polyoxyethylene cetyl alcohol ether, antiseptic, 2-hydroxy-4-methoxybenzophenone, active ingredient (such as lipidure and/or CGS27023A) and fragrance were mixed and prepared to 70° C. (oily phase).

| Preparation Example 3: Milky Liquid | |
|---|---|
| | Wt % |
| Cetyl alcohol | 1.0 |
| Beeswax | 0.5 |
| VASELINE ™ (Petroleum Jelly) | 2.0 |
| Squalene | 6.0 |
| Dimethyl polysiloxane | 2.0 |
| Ethyl alcohol | 5.0 |
| Glycerin | 4.0 |
| 1,3-butylene glycol | 4.0 |
| Active ingredient | 0.1 |
| Tranexamic acid | 1.0 |
| Polyoxyethylene (10) monooleic ester | 1.0 |
| Glycerol monostearic ester | 1.0 |
| Queenseed extract (5% aqueous solution) | 20.0 |
| Antiseptic | As suitable |
| Fragrance | As suitable |
| Ion exchanged water | As suitable |

(Production Method)

Glycerin and 1,3-butylene glycol were added to ion exchanged water, mixed and heated to 70° C. (aqueous phase). Cetyl alcohol, beeswax, VASELINE™ (petroleum jelly), squalene, dimethyl polysiloxane, active ingredient (such as lipidure or CGS27023A), tranexamic acid, polyoxyethylene (10) monooleic ester, glycerol monostearic ester and antiseptic were prepared in the form of a mixture and heated to 70° C. (oily phase). After adding the aqueous phase to the oily phase and performing preliminary emulsification, adding and stirring queenseed extract and ethyl alcohol and obtaining homogeneous emulsified particles using a homomixer, the emulsion was deaerated, filtered and cooled to obtain a milky liquid.

| Preparation Example 4: Milky Liquid | |
|---|---|
| | WT % |
| Cetyl alcohol | 1.0 |
| Beeswax | 0.5 |
| VASELINE ™ (Petroleum Jelly) | 2.0 |
| Squalene | 6.0 |
| Dimethyl polysiloxane | 2.0 |
| Ethyl alcohol | 5.0 |
| Glycerin | 4.0 |
| 1,3-butylene glycol | 4.0 |
| Active ingredient | 0.1 |
| Tranexamic acid | 1.0 |
| Polyoxyethylene (10) monooleic ester | 1.0 |
| Glycerol monostearic ester | 1.0 |
| Queenseed extract (5% aqueous solution) | 20.0 |
| Antiseptic | As suitable |
| Fragrance | As suitable |
| Ion exchanged water | As suitable |

(Production Method)

Glycerin and 1,3-butylene glycol were added to ion exchanged water, mixed and heated to 70° C. (aqueous phase). Cetyl alcohol, beeswax, VASELINE™ (petroleum jelly), squalene, dimethyl polysiloxane, active ingredient (such as lipidure or CGS27023A), tranexamic acid, polyoxyethylene (10) monooleic ester, glycerol monostearic ester and antiseptic were prepared in the form of a mixture and heated to 70° C. (oily phase). After adding the aqueous phase to the oily phase and performing preliminary emulsification, adding and stirring queenseed extract and ethyl alcohol and obtaining homogeneous emulsified particles using a homomixer, the emulsion was deaerated, filtered and cooled to obtain a milky liquid.

After gradually adding the aqueous phase to the oily phase, pre-emulsifying and obtaining homogeneous emulsified particles using a homomixer, the emulsion was deaerated and cooled to obtain a cream.

The invention claimed is:

1. A method for producing artificial skin, the method comprising:
   (a) forming a collagen gel layer containing human fibroblasts;
   (b) culturing epidermal keratinocytes on the collagen gel layer so the keratinocytes adhere to the gel layer to form an epidermal layer; and
   (c) continuing the culturing in an artificial skin forming medium comprising a matrix metalloprotease inhibitor, while exposing the epidermal layer to air,
   wherein the matrix metalloprotease inhibitor is gelatinase inhibitor, collagenase inhibitor, stromelysin inhibitor or matrilysin inhibitor.

2. The method of claim 1, wherein the matrix metalloprotease inhibitor is CGS27023A (N-hydroxy-2-[[(4-methoxyphenyl)sulphonyl]3-pycolyl)-amino]-3-methylbutaneamide hydrochloride) or MMP-inhibitor (p-$NH_2$-Bz-Gly-Pro-D-Leu-Ala-NHOH)(FN-437).

3. A method for producing artificial skin, the method comprising:
   (a) forming a collagen gel layer containing human fibroblasts;
   (b) culturing epidermal keratinocytes on the collagen gel layer so the keratinocytes adhere to the gel layer to form an epidermal layer; and
   (c) continuing the culturing in an artificial skin forming medium comprising a matrix metalloprotease inhibitor and a matrix protein producing promoting agent, while exposing the epidermal layer to air,
   wherein the matrix metalloprotease inhibitor is gelatinase inhibitor, collagenase inhibitor, stromelysin inhibitor or matrilysin inhibitor, and
   wherein the matrix protein production promoting agent is soy bean lysolecithin, transforming growth factor α (TGFa), transforming growth factor β1 (TGFb1), transforming growth factor β2 (TGFb2), transforming growth factor β3 (TGFb3) or epithelial growth factor (EGF).

4. The method of claim 3, wherein the matrix metalloprotease inhibitor is CGS27023A (N-hydroxy-2-[[(4-methoxyphenyl)sulphonyl]3-pycolyl)-amino]-3-methylbutaneamide hydrochloride) or MMP-inhibitor (p-$NH_2$-Bz-Gly-Pro-D-Leu-Ala-NHOH)(FN-437).

* * * * *

UNITED STATES PATENT AND TRADEMARK OFFICE
CERTIFICATE OF CORRECTION

PATENT NO.         : 7,645,595 B2                                                    Page 1 of 1
APPLICATION NO.    : 12/059935
DATED              : January 12, 2010
INVENTOR(S)        : Satoshi Amano et al.

It is certified that error appears in the above-identified patent and that said Letters Patent is hereby corrected as shown below:

Claim 2, column 17, line 25-26:
  delete "methylbutaneamide" and replace with --methylbutanamide--.

Claim 4, column 18, line 23-24:
  delete "methylbutaneamide" and replace with --methylbutanamide--.

Signed and Sealed this

Thirteenth Day of April, 2010

David J. Kappos
*Director of the United States Patent and Trademark Office*